United States Patent
Amschler

(12) 
(10) Patent No.: US 6,211,203 B1
(45) Date of Patent: Apr. 3, 2001

(54) BENZOFURAN-4-CARBOXAMIDES

(75) Inventor: Hermann Amschler, Radolfzell (DE)

(73) Assignee: Byk Gulden Lomberg Chemische Fabrik GmbH, Constance (DE)

(*) Notice: Subject to any disclaimer, the term of this patent is extended or adjusted under 35 U.S.C. 154(b) by 0 days.

(21) Appl. No.: 09/147,640

(22) PCT Filed: Aug. 13, 1997

(86) PCT No.: PCT/EP97/04398
§ 371 Date: Feb. 5, 1999
§ 102(e) Date: Feb. 5, 1999

(87) PCT Pub. No.: WO98/07715
PCT Pub. Date: Feb. 26, 1998

(30) Foreign Application Priority Data

Aug. 19, 1996 (DE) .............................. 196 33 052

(51) Int. Cl.⁷ .................. A61K 31/443; A61K 31/4525; C07D 405/12; C07D 307/78
(52) U.S. Cl. .................... 514/337; 514/469; 514/449; 514/183; 546/284.1; 546/283.4; 546/281.7; 549/429; 549/468; 549/467
(58) Field of Search ............... 546/284.1, 281.7, 546/283.4; 549/429, 456, 462, 467, 468; 514/183, 277, 449, 469, 337

(56) References Cited

U.S. PATENT DOCUMENTS

| | | | |
|---|---|---|---|
| 5,773,467 | * 6/1998 | Dyke et al. | 514/469 |
| 5,925,636 | * 7/1999 | Dyke et al. | 514/242 |
| 5,972,936 | * 10/1999 | Dyke et al. | 514/233.5 |

OTHER PUBLICATIONS

Uspatfull 1999: 132819, RN#192380–97–5, 192380–94–2, 192380–91–9,, 192380–90–8 (see all RN#'s) Dyke et al US 5,972,936, Oct. 1999.*
Uspatfull 1999:81828, RN#192381–05–8, 1923–81–00–3, 192380–98–6, 192380–97–5 (see all RN#'s inthe ref), Dyke et al US 5,925,636, Jul. 1999.*
Uspatfull 1998:75613, RN192381–13–8192381–12–7, 192381–07–0, ( see all the RN#'s in ref) Dyke et al US 5,773,467, Jun. 1998.*

* cited by examiner

Primary Examiner—Alan L. Rotman
Assistant Examiner—Rita Desai
(74) Attorney, Agent, or Firm—Jacobson, Price, Holman & Stern, PLLC

(57) ABSTRACT

Compounds of formula I

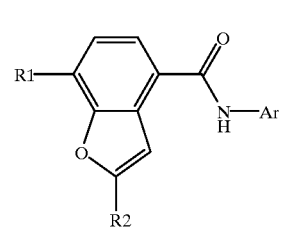

wherein R1 is 1–2C-alkoxy optionally substituted by flourine, R2 is methyl, 1-methylethyl, 3–7C-cycloalkyl or 3–7Ccycloalkylmethyl and Ar is a pyridyl which is optionally di-halo substituted.

20 Claims, No Drawings

BENZOFURAN-4-CARBOXAMIDES

CROSS-REFERENCE

This is a 371 of PCT/EP97/04398 filed Aug. 13, 1997 and claims priority of DE 19633052.1 filed Aug. 19, 1996.

FIELD OF APPLICATION OF THE INVENTION

The invention relates to novel benzofuran-4-carboxamides which are used in the pharmaceutical industry for the production of medicaments.

1. Known Technical Background

International Patent Application WO92/12961 describes benzamides having PDE-inhibiting properties.— International Patent Application WO93125517 discloses trisubstituted phenyl derivatives as selective PDE IV inhibitors.—International Patent Application WO94/02465 describes inhibitors of c-AMP phosphodiesterase and of TNF.—International Patent Application WO95/01338 describes fluoroalkoxy-substituted benzamides and their use as cyclic nucleotide phosphodiesterase inhibitors.— International Patent Application WO97/20833 discloses benzofuran carboxamides and sulphonamides as inhibitors of phosphodiesterase IV.

2. Description of the Invention

It has now been found that the novel benzofuran-4-carboxamides described in greater detail below have surprising and particularly advantageous properties.

The invention thus relates to compounds of the formula I

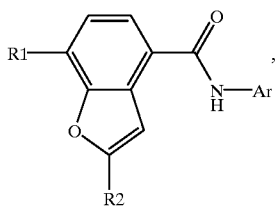

(I)

in which
R1 is 1–2C-alkoxy or 1–2C-alkoxy which is completely or mainly substituted by fluorine,
R2 is 1–7C-alkyl, 3–7C-cycloalkyl or 3–7C-cycloalkylmethyl,
Ar is phenyl, pyridyl, phenyl which is substituted by R3, R4 and R5 or pyridyl which is substituted by R6, R7, R8 and R9, where
  R3 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-atkylcarbonyloxy, amino, mono- or di-1–4C-alkylamino or 1–4C-alkylcarbonylamino,
  R4 is hydrogen, hydroxyl, halogen, amino, trifluoromethyl, 1–4C-alkyl or 1–4C-alkoxy,
  R5 is hydrogen, halogen, 1–4C-alkyl or 1–4C-alkoxy,
  R6 is hydroxyl, halogen, cyano, carboxyl, 1–4C-alkyl, 1–4C-alkoxy, 1–4C-alkoxycarbonyl or amino,
  R7 is hydrogen, halogen, amino or 1–4C-alkyl,
  R8 is hydrogen or halogen and
  R9 is hydrogen or halogen,
the salts of these compounds, and the N-oxides of the pyridines and their salts.

In particular the invention relates to compounds of the formula I, in which
R1 is 1–2C-alkoxy or 1–2C-alkoxy which is completely or mainly substituted by fluorine,
R2 is 1–7C-alkyl, 3–7C-cycloalkyl or 3–7C-cycloalkylmethyl,
Ar is phenyl, pyridyl, phenyl which is substituted by R3, R4 and R5 or pyridyl which is substituted by R6, R7, R8 and R9, where
  R3 is hydroxyl, halogen, cyano, carboxyl, trifluoromethyl, 1–4C-alkyl, 1–4C-alkoxy, 14C-alkoxycarbonyl, 1–4C-alkylcarbonyl, 1–4C-alkylcarbonyloxy, amino, mono- or di-1–4C-alkylamino or 1–4C-alkylcarbonylamino,
  R4 is hydrogen, hydroxyl, halogen, amino, trifluoromethyl, 1–4C-alkyl or 1–4C-alkoxy,
  R5 is hydrogen, halogen, 1–4C-alkyl or 1–4C-alkoxy,
  R6 is hydroxyl, halogen, cyano, carboxyl, 1–4C-alkyl, 1–4C-alkoxy, 1–4C-alkoxycarbonyl or amino,
  R7 is hydrogen, halogen, amino or 1–4C-alkyl,
  R8 is hydrogen or halogen and
  R9 is hydrogen or halogen,
and where R2 is not ethyl or 2,2-dimethylpropyl when R1 is methoxy,
the salts of these compounds, and the N-oxides of the pyridines and their salts.

1–2C-Alkoxy is a radical which, beside the oxygen atom, contains an ethyl radical or preferably a methyl radical.

1–2C-Alkoxy which is completely or mainly substituted by fluorine is, for example, the 1,2,2-trifluoroethoxy, the perfluoroethoxy and in particular the 1,1,2,2-tetrafluoroethoxy, the trifluoromethoxy, the 2,2,2-trifluoroethoxy and preferably the difluoromethoxy radical.

1–7C-Alkyl is straight-chain or branched alkyl radicals having 1 to 7 carbon atoms. Examples are the heptyl, isoheptyl (2-methylhexyl), hexyl, isohexyl (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl, ethyl and the methyl radical.

3–7C-Cycloalkyl is the cyclopropyl, cyclobutyl, cyclopentyl, cyclohexyl and cycloheptyl radical. The 3–5C-cycloalkyl radicals cyclopropyl, cyclobutyl and cyclopentyl are preferred.

3–7C-Cycloalkylmethyl is a methyl radical which is substituted by one of the abovementioned 3–7C-cycloalkyl radicals. The 3–5C-cycloalkylmethyl radicals cyclopropylmethyl, cyclobutylmethyl and cyclopentylmethyl are preferred.

Halogen within the meaning of the present invention is bromine, chlorine and fluorine.

1–4C-Alkyl is straight-chain or branched alkyl radicals having 1 to 4 carbon atoms. Examples are the butyl, isobutyl, sec-butyl, tert-butyl, propyl, isopropyl, ethyl and the methyl radical.

1–4C-Alkoxy is a radical which, beside the oxygen atom, contains one of the abovementioned 14C-alkyl radicals. Examples are the methoxy and the ethoxy radicals.

1–4C-Alkoxycarbonyl is a carbonyl group to which one of the abovementioned 1–4C-alkoxy radicals is bonded. Examples are the methoxycarbonyl ($CH_3O$—CO—) and the ethoxycarbonyl radical ($CH_3CH_2O$—CO—).

1–4C-Alkylcarbonyl is a carbonyl group to which one of the abovementioned 1–4C-alkyl radicals is bonded. An example is the acetyl radical ($CH_3CO$—).

1–4C-Alkylcarbonyloxy radicals, beside the oxygen atom, contain one of the abovementioned 1–4C-alkylcarbonyl radicals. An example is the acetoxy radical ($CH_3CO$—O—).

Examples of mono- or di-1–4C-alkylamino radicals are the methylamino, the dimethylamino and the diethylamino radical.

An example of a 1–4C-alkylcarbonylamino radical is the acetylamido radical (—NH—CO—CH$_3$).

The substituents R3, R4 and R5 can be linked to the phenyl radical in any desired position and combination. Exemplary phenyl radicals substituted by R3, R4 and R5 are the radicals 2-acetylphenyl, 2-aminophenyl, 2-bromophenyl, 2-chlorophenyl, 2,3-dichlorophenyl, 2,4-dichlorophenyl, 4-diethylamino-2-methylphenyl, 4-bromo-2-trifluoromethylphenyl, 2-carboxy-5-chlorophenyl, 3,5-dichloro-2-hydroxyphenyl, 2-bromo-4-carboxy-5-hydroxyphenyl, 2,6-dichlorophenyl, 2,5-dichlorophenyl, 2,4,6-trichlorophenyl, 2,4,6-trifluorophenyl, 2,6-dibromophenyl, 2-cyanophenyl, 4-cyano-2-fluorophenyl, 2-fluorophenyl, 2,4-difluorophenyl, 2,6-difluorophenyl, 2-chloro-6-fluorophenyl, 2-hydroxyphenyl, 2-hydroxy-4-methoxyphenyl, 2,4-dihydroxyphenyl, 2-methoxyphenyl, 2,3-dimethoxyphenyl, 2,4-dimethoxyphenyl, 2,6-dimethoxyphenyl, 2-dimethylaminophenyl, 2-methylphenyl, 2-chloro-6-methylphenyl, 2,4-dimethylphenyl, 2,6-dimethylphenyl, 2,3-dimethylphenyl, 2-methoxycarbonylphenyl, 2-trifluoromethylphenyl, 2,6-dichloro-4-methoxyphenyl, 2,6-dichloro-4-cyanophenyl, 2,6-dichloro-4-aminophenyl, 2,6-dichloro-4-methoxycarbonylphenyl, 4-acetylamino-2,6-dichlorophenyl, 2,6-dichloro-4-ethoxycarbonylphenyl, 4-carboxyphenyl and 4-carboxy-2,6-dichlorophenyl.

The substituents R6, R7, R8 and R9 can be linked to the pyridyl ring in any desired position and combination. Exemplary pyridyl radicals substituted by R6, R7, R8 and R9 are the radicals 3,5-dichloropyrid-4-yl, 2,6-diaminopyrid-3-yl, 4-aminopyrid-3-yl, 3-methylpyrid-2-yl, 4-methylpyrid-2-yl, 5-hydroxypyrid- 2-yl, 4-chloropyrid-3-yl, 3-chloropyrid-2-yl, 3-chloropyrid-4-yl, 2-chloropyrid-3-yl, 2,3,5,6-tetrafluoropyrid-4-yl, 3,5-dichloro-2,6-difluoropyrid-4-yl, 3,5-dibromo-pyrid-2-yl, 3,5-dibromopyrid-4-yl, 3,5-dichloropyrid-4-yl, 2,6-dichloropyrid-3-yl, 3,5-dimethylpyrid-4-yl, 3-chloro-2,5,6-trifluoropyrid-4-yl and 2,3,5-trifluoropyrid-4-yl.

Compounds of the formula I to be emphasized are those in which
R1 is 1–2C-alkoxy or 1–2C-alkoxy which is completely or mainly substituted by fluorine,
R2 is 1–7C-alkyl, 3–7C-cycloalkyl or 3–7C-cycloalkylmethyl,
Ar is phenyl, pyridyl, phenyl substituted by R3, R4 and R5 or pyridyl substituted by R6, R7, R8 and R9, where
R3 Is halogen, carboxyl or 1–4C-alkoxycarbonyl,
R4 is hydrogen or halogen,
R5 is hydrogen or halogen,
R6 is halogen,
R7 is hydrogen or halogen, and
R8 and R9 are hydrogen,
the salts of these compounds, and the N-oxides of the pyridines and their salts.

Preferred compounds of the formula I to be emphasized are those in which
R1 is 1–2C-alkoxy or 1–2C-alkoxy which is completely or mainly substituted by fluorine,
R2 is 1–7C-alkyl, 3–7C-cycloalkyl or 3–7C-cycloalkylmethyl,
Ar is phenyl, pyridyl, phenyl substituted by R3, R4 and R5 or pyridyl substituted by R6, R7, R8 and R9, where
R3 is halogen, carboxyl or 1–4C-alkoxycarbonyl,
R4 is hydrogen or halogen,
R5 is hydrogen or halogen,
R6 is halogen,
R7 is hydrogen or halogen, and
R8 and R9 are hydrogen,
and where R2 is not ethyl or 2,2-dimethylpropyl when R1 is methoxy,
the salts of these compounds, and the N-oxides of the pyridines and their salts.

Compounds of the formula I which are particularly to be emphasized are those in which
R1 is 1–2C-alkoxy or 1–2C-alkoxy which is completely or mainly substituted by fluorine,
R2 is 1–4C-alkyl or 3–5C-cycloalkyl, and
Ar is pyridyl, 3,5-dichloropyrid-4-yl, 2,6-difluorophenyl, 4-carboxy-2,6-dichlorophenyl, 4-carboxyphenyl, 4-methoxycarbonylphenyl, 4-ethoxycarbonylphenyl, 2,6-dichloro-4-methoxycarbonylphenyl or 2,6-dichloro-4-ethoxycarbonylphenyl,
the salts of these compounds, and the N-oxides of the pyridines and their salts.

Preferred compounds of the formula I which are particularly to be emphasized are those in which
R1 is 1–2C-alkoxy or 1–2C-alkoxy which is completely or mainly substituted by fluorine,
R2 is 1–4C-alkyl or 3–5C-cycloalkyl, and
Ar is pyridyl, 3,5-dichloropyrid-4-yl, 2,6-difluorophenyl, 4-carboxy-2,6-dichlorophenyl, 4-carboxyphenyl, 4-methoxycarbonylphenyl, 4-ethoxycarbonylphenyl, 2,6-dichloro-4-methoxycarbonylphenyl or 2,6-dichloro-4-ethoxycarbonylphenyl,
and where R2 is not ethyl when R1 is methoxy,
the salts of these compounds, and the N-oxides of the pyridines and their salts.

Preferred compounds of the formula I are those in which
R1 is difluoromethoxy and
R2 is 1–4C-alkyl or 3–5C-cycloalkyl
or
R1 is methoxy and
R2 is 1–4C-alkyl or 3–5C-cycloalkyl
or
R1 is 1–2C-alkoxy or 1–2C-alkoxy which is completely or mainly substituted by fluorine and
R2 is methyl, isopropyl or cyclopentyl and
Ar is pyridyl, 3,5-dichloropyrid-4-yl, 2,6-difluorophenyl, 4-carboxy-2,6dichlorophenyl, 4-carboxyphenyl, 4-methoxycarbonylphenyl, 4-ethoxycarbonylphenyl, 2,6-dichloro-4-methoxycarbonylphenyl or 2,6-dichloro-4-ethoxycarbonylphenyl,
the salts of these compounds, the N-oxides of the pyridines and their salts.

Particularly preferred compounds of the formula I are those in which
R1 is difluoromethoxy,
R2 is 1–4C-alkyl or 3–5C-cycloalkyl and
Ar is 3,5-dichloropyrid-4-yl, 2,6-dichloro4-methoxycarbonylphenyl or 4-carboxy-2,6-dichlorophenyl
or
R1 is methoxy,
R2 is 1–4C-alkyl or 3–5C-cycloalkyl and
Ar is 3,5-dichloropyrid-4-yl, 4-pyridyl, 2,6-dichloro-4-methoxycarbonylphenyl or 4-carboxy-2,6-dichlorophenyl
or
R1 is methoxy, ethoxy or difluoromethoxy and
R2 is methyl, isopropyl or cyclopentyl and
Ar is 3,5-dichloropyridyl, 4-pyridyl, 2,6-dichloro-4-methoxycarbonylphenyl or 4-carboxy-2,6dichlorophenyl,
the salts of these compounds, the N-oxides of the pyridines and their salts.

Suitable salts of compounds of the formula I—depending on substitution—are all acid addition salts or all salts with bases. The pharmacologically tolerable salts of the inorganic and organic acids and bases customarily used in pharmacy may be mentioned particularly. Those suitable are on the one hand water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

On the other hand, salts with bases are also especially suitable. Examples of salts with bases are alkali metal (lithium, sodium, potassium) or calcium, aluminum, magnesium, titanium, ammonium, meglumine or guanidinium salts, here also in salt preparation the bases being employed in an equimolar quantitative ratio or one differing therefrom.

Pharmacologically intolerable salts which can be initially obtained, for example, as process products in the preparation of the compounds according to the invention on an industrial scale, are converted into pharmacologically tolerable salts by processes known to the person skilled in the art.

The invention further relates to compounds of the formula II

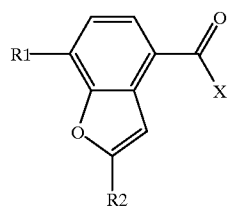

(II)

in which R1 and R2 have the meanings indicated above and X is a leaving group such as, for example, halogen.

The invention further relates to a process for the preparation of the compounds of the formula I and their salts, and also the N-oxides of the pyridines and their salts. The process comprises reacting compounds of the formula II, in which R1 and R2 have the meanings indicated above and X is a suitable leaving group, with amines $H_2N$—Ar, in which Ar has the meaning indicated above, and, if desired, then converting compounds of the formula I obtained into their salts and/or converting pyridines obtained into the N-oxides and, if desired, then converting into the salts, or, if desired, then converting salts of the compounds of the formula I obtained into the free compounds. If desired, compounds of the formula I obtained can be converted into further compounds of the formula I by derivatization. This can be carried out, for example, as described in the examples by the hydrolysis of ester groups to the corresponding acids.

The person skilled in the art is familiar on the basis of his expert knowledge with suitable leaving groups X. For example, suitable starting materials are acid halides of the formula II (X=Cl or Br). Otherwise, the reaction is carried out, for example, as described in the following examples, or in a manner familiar perse to the person skilled in the art (e.g. as described in the International Patent Application WO92/12961).

The N-oxidation is carried out in a manner which is likewise familiar to the person skilled in the art, e.g. with the aid of m-chloroperoxybenzoic acid in dichloromethane at room temperature. The person skilled in the art is familiar on the basis of his expert knowledge with reaction conditions which are specifically necessary for carrying out the process.

The isolation and purification of the substances according to the invention is carried out in a manner know per se, for example, by distilling off the solvent in vacuo and recrystallizing the residue obtained from a suitable solvent or subjecting it to one of the customary purification methods, such as, for example, column chromatography on suitable carrier material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a nonsolvent for the addition salt or by evaporating the solvent.

Salts obtained can be converted by basification or by acidification into the free compounds, which can in turn be converted into salts. In this manner, pharmacologically intolerable salts can be converted into pharmacologically tolerable salts.

The amines $H_2N$—Ar, in which Ar has the meaning indicated above, are either known, or they can be prepared in a manner known to the person skilled in the art.

Compounds of the formula II in which R1 and R2 have the meanings indicated above can be prepared from corresponding compounds of the formula III

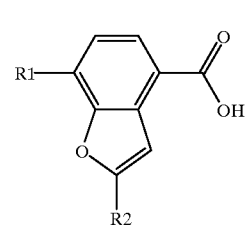

(III)

by use of methods known to the person skilled in the art. If X in the formula II has the meaning chlorine, this can be carried out, for example, as described in the examples by reaction of the compounds of the formula III with thionyl chloride.

Compounds of the formula III are accessible from the-corresponding compounds of the formula IV

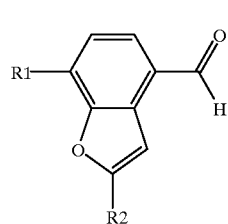

(IV)

or from the corresponding compounds of the formula V

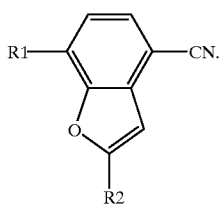

(V)

For example, compounds of the formula V in which R1 and R2 have the meanings indicated above are hydrolyzed using alkali metal hydroxides (optionally with addition of hydrogen peroxide) or appropriately substituted compounds of the formula IV in which R1 and R2 have the meanings indicated above are oxidized to the compounds III (e.g. as described in J. Org. Chem. 1986, 51, 569–571).

The compounds of the formulae IV and V in which R1 and R2 have the meanings indicated above are accessible (e.g. as described in Chem. Pharm. Bull. 1992, 40(5), 1148–1153 and Chem. Pharm. Bull. 1992, 40(8), 2002–2006) by a cesium fluoride-mediated Claisen rearrangement of the appropriately substituted compounds of the formula VI

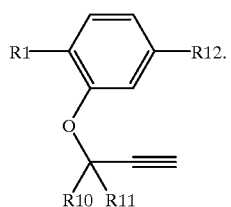

(VI)

In the compounds of the formula VI, R1 has the meaning indicated above and R12 is cyano or formyl. The substituents R10 and R11 together with the carbon atom to which they are bonded form the corresponding substituent R2 after the Claisen rearrangement to the compounds of the formulae IV and V.

The compounds of the formula V can also be obtained from the appropriately substituted compounds of the formula IV by reaction with hydroxylamine in formic acid (e.g. as described in Synthesis 1979, 2, 112–113).

The compounds of the formula VI are either known or can be prepared in a manner known to the person skilled in the art, as described, for example, in Tetrahedron Lett. 1994, 35, 6405–6408.

The following examples serve to Illustrate the invention in greater detail without restricting it. Further compounds of the formulae I and II, whose preparation is not described explicitly, can also be prepared in an analogous manner or in a manner familiar per se to the person skilled in the art using customary process techniques.

In the examples, m.p. is melting point, b.p. is boiling point, h is hour(s), RT is room temperature. The compounds and their salts, and the N-oxides of the pyridines and their salts mentioned in the examples are a preferred subject of the invention.

EXAMPLES

Final products

1. N-(3,5-Dichloropyrid-4-yl)-7-methoxy-2-methylbenzofuran-4-carboxamide 1.5 g of sodium hydride (80% strength) were added in small portions to a solution of 4.1 g of 4-amino3,5-dichloropyridine in 50 ml of tetrahydrofuran and the suspension was stirred for about 0.5 h until evolution of hydrogen had ended. In parallel to this, 4.1 g of 7-methoxy-2-methylbenzofuran-4-carboxylic acid was stirred at 80° C. for 3 h with 7.25 ml of thionyl chloride in 40 ml of toluene and the mixture was then evaporated in vacuo. About 20 ml of toluene were added to the residue and the solution was evaporated again in vacuo. The residue was then taken up in 50 ml of tetrahydrofuran and this solution was added dropwise at RT to the prepared suspension. After reaction was complete, the mixture was stirred into about 200 ml of ice water, treated with 30 ml of 2 N hydrochloric acid and extracted with ethyl acetate. This extract was dried over calcined sodium sulfate and evaporated in vacuo. The residue was crystallized from ethyl acetate/petroleum spirit (b.p. 50–80° C.): m.p. 233° C.

Starting from the starting compounds described below, the final products described below are obtained by reaction of the corresponding benzofuran-4-carboxylic acids of the formula III with 4-amino-3,5-dichloropyridine or 4-aminopyridine analogously to Example 1:

2. N-(3,5-Dichloropyrid-4-yl)-7-methoxy-2-(1-methylethyl)benzofuran-4-carboxamide M.p. 193° C.

3. N-(3,5-Dichloropyrid-4-yl)-7-methoxy-2-(1-methylethyl)benzofuran-4-carboxamide M.p. 180° C.

4. N-(3,5-Dichloropyrid-4-yl)-7-difluoromethoxy-2-(1-methylethyl)benzofuran-4-carboxamide M.p. 157° C.

5. N-(3,5-Dichloropyrid-4-yl)-2-cyclopentyl-7-methoxybenzofuran-4-carboxamide M.p. 174–175° C.

6. 7-Methoxy-2-(methylethyl)-N-(4-pyridyl)benzofuran-4-carboxamide M.p. 186° C.

7. N-(2,6-Dichloro-4-methoxycarbonylphenyl)-7-methoxy-2-(1-methylethyl)benzofuran-4-carboxamide 2.0 g of triethylamine were added to a solution of 4.4 g of methyl 4-amino-3,5-dichlorobenzoate in 50 ml of tetrahydrofuran and the mixture was stirred (solution 1). In parallel to this, 4.7 g of 7-methoxy-2-(1-methylethyl)benzofuran-4-carboxylic acid were stirred at 80° C. for 3 h with 10.0 ml of thionyl chloride in 40 ml of toluene and the mixture was then evaporated in vacuo. About 20 ml of toluene were added to the residue and the solution was evaporated again in vacuo. The residue was then taken up in 50 ml of tetrahydrofuran and this solution was added dropwise at RT to the prepared solution 1. After reaction was complete, the mixture was stirred into about 200 ml of ice water, treated with 30 ml of 2 N hydrochloric acid and extracted with ethyl acetate. This extract was dried over calcined sodium sulfate and evaporated in vacuo. The residue was crystallized from toluene: m.p. 175° C.

The following compound was prepared according to Example 7 from the appropriately substituted benzofuran-4-carboxylic acid of the formula III:

8. N-(2,6-Dichloro-4-methoxycarbonylphenyl)-7-difluoromethoxy-2-(1-methylethyl)benzofuran-4-carboxamide M.p. 186° C.

9. N-(2,6-Dichloro-4-carboxyphenyl)-7-methoxy-2-(1-methylethyl)benzofuran-4-carboxamide 3.7 g of N-(2,6-Dichloro-4-methoxycarbonylphenyl)-7-methoxy-2-(1-methylethyl)benzofuran-4-carboxamide are refluxed for 15 min. in 20 ml of diethylene glycol and 30 ml of water in which 0.41 g of caustic soda is dissolved. The solution is diluted with water and acidified to pH 2 using 2 N sulfuric acid. The product precipitates in this process. It is filtered off with suction on a suction filter, washed free of acid with water and dried in vacuo: m.p. 279° C.

The compound of Example 8 is hydrolyzed in accordance with Example 9:

10. N-(2,6-Dichloro-4-carboxyphenyl)-7-difluoromethoxy-2-(1-methylethyl)benzofuran-4-carboxamide M.p. 272° C.
Starting compounds A. 7-Difluoromethoxy-2-(1-methylethyl)benzofuran-4-carboxylic acid A solution of 0.88 g of sodium chlorite in 5 ml of water is added dropwise to 1.6 g of 7-difluoromethoxy-2-(1-methylethyl)benzofuran-4-carbaldehyde and 0.83 g of amidosulfuric acid dissolved in 15 ml of glacial acetic acid such that the Internal temperature is kept between 15 and 20° C. The mixture is stirred for a further 1 h and then poured into 150 ml of ice water, and the precipitate formed is filtered off with suction and washed free of acid with water. For purification, the crude product is dissolved in half-concentrated, aqueous ammonia, and the aqueous solution is extracted with toluene and acidified to pH 1–2 using 2 N hydrochloric acid. The precipitate formed is filtered off with suction, washed free of acid with water and dried in vacuo: m.p. 169° C.

The following is prepared in the same manner starting from the corresponding benzofuran-4-carbaldehyde of the formula IV:

B. 7-Methoxy-2-(1-methylethyl)benzofuran-4-carboxlic acid M.p. 166° C.

C. 7-Ethoxy-2-1-methylethyl)benzofuran-4-carboxylic acid 0.5 g of 7-ethoxy-2-(1-methylethyl)benzofuran-4-carbonitrile is refluxed for 5 h in a solution of 10 ml of n-butanol, 30 ml of sodium hydroxide solution (50% strength) and 2.5 ml of hydrogen peroxide (30% strength). The mixture is then diluted with ice water, acidified to pH 1–2 using 2 N hydrochloric acid and the precipitate formed is filtered off with suction, washed free of acid with water and dried in vacuo: m.p. 186° C.

The following are prepared in the same manner starting from appropriate benzofuran-4-carbonitrites of the formula V:

D. 7-Methoxy-2-methylbenzofuran4-carboxylic acid M.p. 247° C.

E. 7-Methoxy-2-cyclopentylbenzofuran-carboxylic acid M.p. 170–171° C.

F. 7-Difluoromethoxy-2-(1-methylethyl)benzofuran4-carbaldehyde 5.5 g of 4-difluoromethoxy-3-(2-methyl-3-butyn-2-yloxy)benzaldehyde are refluxed with 7.2 g of cesitum fluoride for 12 h with nitrogen aeration in 30 ml of N,N-diethylaniline. After cooling, the mixture is stirred into 300 ml of 4 N hydrochloric acid, the resulting emulsion is extracted three times with 50 ml of ethyl acetate, and the organic extracts are combined, dried over calcined potassium carbonate and evaporated in vacuo. The residue is chromatographed on silica gel using toluene. After evaporating the appropriate fractions, the title compound is obtained as an oil.

The following are obtained in the same manner Starting from the corresponding benzaldehydes of the formula VI:

G. 7-Methoxy-2-(1-methylethyl)benzofuran-4-carbaldehyde Oil.

H. 7-Methoxy-2-cyclopentylbenzofuran-4-carbaldehyde oil.

I. 7-Methoxy-2-methylbenzofuran-4-carbaldehyde M.p. 69° C.

J. 7-Methoxy-2-methylbenzofuran-4-carbonitrile 27.6 g of 7-methoxy-2-methylbenzofuran-4-carbaldehyde are refluxed in 250 ml of formic acid for 1.5 h with 11.6 g of hydroxylamine and 19.7 g of sodium formate. The cooled solution is stirred into about 1.5 l of ice water, and the precipitate is filtered off with suction through a frit, washed free of acid with water and dried in vacuo: m.p. 103° C.

The following is prepared in the same manner starting from the corresponding benzofuran-4-carbaldehyde of the formula IV:

K. 2-Cyclopentyl-7-methoxybenzofuran-4-carbonitrile Oil.

L. 7-Methoxy-2-(1-methylethyl)benzofuran-4-carbonitrile 5.3 g of 3-(1,1-dimethylprop-2-yn-1-yloxy)-4-methoxybenzonitrile and 5.3 g of cesium fluoride are refluxed for 12 h in 30 ml of N,N-diethylaniline with nitrogen aeration. After cooling, the mixture is stirred into 300 ml of 4 N hydrochloric acid, the resulting emulsion is extracted three times with 5.0 ml of ethyl acetate, and the organic extracts are combined, dried over calcined potassium carbonate and evaporated in vacuo. The residue is chromatographed on silica gel using toluene. After evaporating the corresponding fractions, the title compound is obtained as an oil.

The following is prepared in the same manner starting from 3-(1,1-dimethylprop-2-yn-1-yloxy)-4-ethoxybenzonitrile:

M. 7-Ethoxy-2-(1-methylethyl)benzofuran-4-carbonitrile Oil.

N. 4-Difluoromethoxy-3-(2-methyl-3-butyn-2-yloxy)benzaldehyde
Solution 1

19.0 g of 2-methyl-3-butyn-2-ol are dissolved in 60 ml of dry acetonitrile with nitrogen aeration, the mixture is cooled to −5° C. using ice/salt, 22.8 g of 1,8-diazabicyclo[5.4.0]undec-7-ene (DBU) are added, the mixture is stirred at −5° C. for 10 min. and then 24.4 g of trifluoroacetic anhydride are added dropwise such that the temperature of the solution is kept below 0° C. After addition is complete, the solution is stirred at −5° to −2° C. for a further 30 min.
Solution 2

18.1 g of 4-difluoromethoxy-3-hydroxybenzaldehyde are dissolved in 60 ml of dry acetonitrile with nitrogen aeration, cooled to −5° C. with ice/salt, 0.01 g of copper(I) chloride and 19.8 g of DBU are added and the mixture is stirred at −5° C. for a further 30 min.

Solution 1 is then added dropwise to solution 2 in the course of 40 min. with stirring at −5° C. and the mixture is stirred at 0° C. for 5 h. The mixture is then evaporated in vacuo, the residue is taken up in 100 ml of water and the solution is extracted three times with 200 ml of toluene each time. The combined toluene extracts are washed successively with three times 50 ml of 1 N hydrochloric acid, two times 50 ml of 1 N sodium hydroxide solution, 50 ml of saturated sodium bicarbonate solution and finally with 50 ml of saturated sodium chloride solution, dried over calcined magnesium sulfate and concentrated in vacuo, and the residue is chromatographed on silica gel using a mixture of cyclohexane/ethanol (97:3). After evaporating the appropriate fractions 4-difluoromethoxy-3-(2-methyl-3-butyn-2-yloxy)benzaldehyde is obtained as an oil.

In the same manner, 3-hydroxy-4-methoxybenzaldehyde and 4-ethoxy-3-hydroxybenzaldehyde are reacted with appropriate 1-ethynyl alcohols according to Example M:

O. 3-(2-Methyl-3-butyn-2-yloxy)-4-methoxybenzaldehyde Oil

P. 3(1-Ethynylcyclopentyloxy)-4-methoxybenzaldehyde M.p. 91.5–93° C.

Q. 4-Methoxy-3-(2-propyn-1-yloxy)benzaldehdye M.p. 74.5° C.

The following benzonitriles of the formula VI are prepared in the same manner from 3-hydroxy-4-methoxybenzonitrile or 4-ethoxy-3-hydroxybenzonitrile:

R. 3-(1,1-Dimethylprop-2-yn-1-yloxy)-4-methoxybenzonitrile M.p. 103° C.

S. 4-Ethoxy-3-(1,1-dimethylprop-2-yn-1-yloxy) benzonitrile M.p. 60° C.

T. 3-(1-Ethynyl-1-cyclopentyloxy)-4-methoxybenzonitrile Mp. 67° C.

Commercial utility

The compounds according to the invention have useful pharmacological properties which make them commercially utilizable. As selective cyclic nucleotide phosphodiesterase (PDE) inhibitors (namely of type IV), they are suitable on the one hand as bronchial therapeutics (for the treatment of airway obstructions on account of their dilating action but also on account of their respiratory rate- or respiratory drive-increasing action) and for the rectification of erectile dysfunction on account of the vasodilating action, but on the other hand especially for the treatment of disorders, in particular of inflammatory nature, e.g. of the airways (asthma prophylaxis), of the skin, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. The compounds according to the invention are distinguished here by a low toxicity, a good enteral absorption (high bioavailability), a wide therapeutic range and the absence of significant side effects.

On account of their POE-inhibiting properties, the compounds according to the invention can be employed in human and veterinary medicine as therapeutics, it being possible to use them, for example, for the treatment and prophylaxis of the following diseases: acute and chronic (in particular inflammatory and allergen-induced) airway disorders of various origin (bronchitis, allergic bronchitis, bronchial asthma); dermatoses (in particular of proliferative, inflammatory and allergic, nature) such as, for example, psoriasis (vulgaris), toxic and allergic contact eczema, atopic eczema, seborrheic eczema, lichen simplex, sunburn, pruritus in the anogenital region, alopecia areata, hypertrophic scars, discoid lupus erythematosus, follicular and wide-spread pyodermias, endogenous and exogenous acne, acne rosacea, and other proliferative, inflammatory and allergic skin disorders; disorders which are based on an excessive release of TNF and leukotrienes, e.g. disorders of the arthritic type (rheumatoid arthritis, rheumatoid spondylitis, osteoarthritis and other arthritic conditions), disorders of the immune system (AIDS, multiple sclerosis), types of shock [septic shock, endotoxin shock, gram-negative sepsis, toxic shock syndrome and ARDS (adult respiratory distress syndrome)], and generalized inflammations in the gastrointestinal region (Crohn's disease and ulcerative colitis); disorders which are based on allergic and/or chronic, faulty immunological reactions in the region of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxing action of the PDE inhibitors, such as, for example, erectile dysfunction or colics of the kidneys and of the ureters in connection with kidney stones; or alternatively disorders of the CNS, such as, for example, depressions or arteriosclerotic dementia.

The invention further relates to a method for the treatment of mammals, including humans, which are suffering from one-of the abovementioned diseases. The method comprises administering to the sick mammal a therapeutically active and pharmacologically tolerable amount of one or more of the compounds according to the invention.

The invention further relates to the compounds according to the invention for use in the treatment and/or prophylaxis of the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned, which contain one or more of the compounds according to the invention.

The medicaments are prepared by processes known per se which are familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on account of his expert knowledge with the auxiliaries which are suitable for the desired pharmaceutical formulations. Beside solvents, gel-forming agents, ointment bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. To this end, these are either administered directly as powders (preferably in micronized form) or by atomizing solutions or supsensions which contain them. With respect to the preparations and administration forms, reference is made, for example, to the details in European Patent 163 965.

For the treatment of dermatoses, the administration of the compounds according to the invention is in particular carried out in the form of those medicaments which are suitable for topical application. For the production of the medicaments, the compounds according to the invention (=active compounds) are preferably mixed with suitable pharmaceutical auxiliaries and processed further to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by methods known per se. The dosage of the active compounds is carried out in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 1 mg per puff. The customary dose in the case of systemic therapy (p.o. or i.v.) is between 0.1 and 200 mg per application.

Biological investigations

In the investigation of PDE IV inhibition at the cellular level, the activation of inflammatory cells is ascribed particular importance. An example is the FMLP (N-formyl-methionyl-leucyl-phenylalanine)-induced superoxide production of neutrophilic granulocytes, which can be measured as luminol-potentiated chemoluminescence. [Mc Phail L C, Strum S L, Leone P A and Sozzani S, The neutrophil respiratory burst mechanism. In "Immunology Series" 1992, 57, 47–76; ed. Coffey R G (Marcel Decker, Inc., New York-Basle-Hong Kong)].

Substances which inhibit chemoluminescence and cytokine secretion and the secretion of proinflammatory mediators of inflammatory cells, in particular neutrophilic and eosinophilic granulocytes, are those which inhibit PDE IV. This isoenzyme of the phosphodiesterase families is particularly represented in granulocytes. Its inhibition leads to the raising of the intracellular cyclic AMP concentration and thus to the inhibition of cellular activation. PDE IV inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma?. Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE III/IV inhibitor. In "New Drugs for Asthma Therapy", 379–402, Birkhäuser Veriag Basle 1991; Schudt C et al., Influence of selective phospho-diesterase inhibitors on human neutrophil functions and levels of cAMP and $Ca_i$. Naunyn-Schmiedebergs Arch Pharmacol 1991, 344, 682–690; Nielson C P et al., Effects of selective phosphodiesterase inhibitors on polymorphonuclear leucocyte respiratory burst. J Allergy Clin Immunol 1990, 86, 801–808; Schade et al., The specific type III and IV phosphodiesterase inhibitor zardaverine suppress formation of tumor necrosis factor by macrophages. European Journal of Pharmacology 1993, 230, 9–14).

1. Inhibition of PDE IV activity

Methodology

The activity test was carried out according to the method of Bauer and Schwabe, which was adapted to microtiter plates (Naunyn-Schmiedeberg's Arch. Pharmacol. 1980, 311,1.93–198). Here the PDE reaction takes place in the first step. In a second step, the 5'-nucleotide formed is cleaved to the uncharged nucleoside by a 5'-nucleotidase of the snake venom of *Ophiophagus hannah* (king cobra). In the third step, the nucleoside is separated from the remaining charged substrate on ion-exchange columns. The columns are eluted with 2 ml of 30 mM ammonium formate (pH 6.0) directly into minivials to which is additionally added 2 ml of scintillator fluid for counting.

The inhibitory values determined for the compounds according to the invention can be seen from the following Table A, in which the numbers of the compounds correspond to the numbers of the examples.

TABLE A

| Inhibition of PDE IV activity | |
| --- | --- |
| Compound | -log IC$_{50}$ |
| 1 | 8.42 |
| 2 | 9.28 |
| 3 | 8.18 |
| 4 | 9.72 |
| 5 | 8.80 |

What is claimed is:

1. A compound of formula I

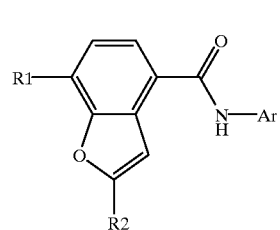

in which

R1 is 1–2C-alkoxy or 1–2C-alkoxy which is completely or mainly substituted by fluorine, R2 is methyl, 1-methylethyl, 3–7C-cycloalkyl or 3–7C-cycloalkylmethyl, Ar is pyridyl which is optionally dihalo-substituted;

a salt thereof, an N-oxide of a pyridine thereof, or a salt of the latter.

2. A compound of claim 1 wherein R1 is methoxy, a salt thereof, an N-oxide of a pyridine thereof, or a salt of the latter.

3. A compound of claim 2 wherein R2 is methyl, a salt thereof, an N-oxide of a pyridine thereof, or a salt of the latter.

4. A compound of claim 3 wherein Ar is 3,5-dichloropyrid-4-yl, a salt thereof, an N-oxide of a pyridine thereof, or a salt of the latter.

5. A compound of claim 2 wherein R2 is 1-methylethyl, a salt thereof, an N-oxide of a pyridine thereof, or a salt of the latter.

6. A compound of claim 5 wherein Ar is 3,5-dichloropyrid-4-yl, a salt thereof, an N-oxide of a pyridine thereof, or a salt of the latter.

7. A compound of claim 5 wherein Ar is 4-pyridyl, a salt thereof, an N-oxide of a pyridine thereof, or a salt of the latter.

8. A compound of claim 3 wherein R2 is cyclopentyl, a salt thereof, an N-oxide of a pyridine thereof, or a salt of the latter.

9. A compound of claim 8 wherein Ar is 3,5-dicloropyrid-4-yl, a salt thereof, an N-oxide of a pyridine thereof, or a salt of the latter.

10. A compound of claim 1 wherein R1 is difluoromethoxy, a salt thereof, an N-oxide of a pyridine thereof, or a salt of the latter.

11. A compound of claim 10 wherein R2 is 1-methylethyl, a salt thereof, an N-oxide of a pyridine thereof, or a salt of the latter.

12. A compound of claim 11 wherein Ar is 3,5-dichloropyrid-4-yl, a salt thereof, an N-oxide of a pyridine thereof, or a salt of the latter.

13. A compound of claim 1 wherein R1 is ethoxy, a salt thereof, an N-oxide of a pyridine thereof, or a salt of the latter.

14. A compound of claim 13 wherein R2 is 1-methylethyl, a salt thereof, an N-oxide of a pyridine thereof, or a salt of the latter.

15. A compound of claim 14 wherein Ar is 3,5-dichloropyrid-4-yl, a salt thereof, an N-oxide of a pyridine thereof, or a salt of the latter.

16. A compound of claim 1 wherein R2 is 3–7C-cycloalkyl; a salt thereof, and N-oxide of a pyridine thereof, or a salt of the latter.

17. A compound of claim 1 wherein R2 is 3–7C-cycloalkylmethyl; a salt thereof, and N-oxide of a pyridine thereof, or a salt of the latter.

18. A pharmaceutical composition suitable for treating a disorder of the respiratory tract or a disorder of inflammatory nature, and comprising a suitable carrier and an effective amount of a pharmaceutically-acceptable compound, which is a compound as claimed in claim 1, a salt thereof, an N-oxide of a pyridine thereof, or a salt of the latter.

19. In a method of treating a disorder of the respiratory tract or a disorder of inflammatory nature, which comprises administering an effective amount of a suitable pharmaceutically-acceptable active ingredient to a subject so afflicted, the improvement wherein the pharmaceutically-acceptable active ingredient is a compound as claimed in claim 1, a salt thereof, an N-oxide of a pyridine thereof, or a salt of the latter.

20. In a method of compounding a pharmaceutical composition by admixing with a suitable carrier an effective amount of a pharmaceutically-acceptable active component suitable for treating a disorder of the respiratory tract or a disorder of inflammatory nature, the improvement wherein the pharmaceutically-acceptable active component is a compound as claimed in claim 1, a salt thereof, an N-oxide of a pyridine thereof, or a salt of the latter.

\* \* \* \* \*